(12) United States Patent
Crombie et al.

(10) Patent No.: US 10,786,791 B1
(45) Date of Patent: Sep. 29, 2020

(54) SYSTEM AND METHOD FOR HARVESTING EMULSIFIED FAT AND STEM CELLS

(71) Applicant: Black Tie Medical, Inc., San Diego, CA (US)

(72) Inventors: John Crombie, East Hanover, NJ (US); Mary Pilkington, San Diego, CA (US); Mariano Riego de Dios, San Diego, CA (US)

(73) Assignee: Black Tie Medical, Inc., San Diego, CA (US)

( * ) Notice: Subject to any disclaimer, the term of this patent is extended or adjusted under 35 U.S.C. 154(b) by 291 days.

(21) Appl. No.: 15/682,892

(22) Filed: Aug. 22, 2017

Related U.S. Application Data

(62) Division of application No. 14/846,357, filed on Sep. 4, 2015, now Pat. No. 10,279,325.

(60) Provisional application No. 62/045,926, filed on Sep. 4, 2014.

(51) Int. Cl.
| | | |
|---|---|---|
| *B01F 5/06* | (2006.01) |
| *B01F 3/08* | (2006.01) |
| *C12N 5/077* | (2010.01) |
| *A61L 27/36* | (2006.01) |
| *A61L 27/50* | (2006.01) |

(52) U.S. Cl.
CPC ........ *B01F 5/0685* (2013.01); *A61L 27/3604* (2013.01); *A61L 27/3691* (2013.01); *A61L 27/50* (2013.01); *B01F 3/0807* (2013.01); *C12N 5/0653* (2013.01); *A61L 2300/64* (2013.01); *A61L 2400/06* (2013.01); *B01F 2215/0034* (2013.01); *C12N 2509/10* (2013.01)

(58) Field of Classification Search
CPC .. A61L 27/3604; A61L 27/3691; A61L 27/50; A61L 2400/06; A61L 2300/64
See application file for complete search history.

(56) References Cited

U.S. PATENT DOCUMENTS

| | | | | |
|---|---|---|---|---|
| 4,753,634 A * | 6/1988 | Johnson | ................. | A61B 17/34 |
| | | | | 210/406 |
| 5,002,538 A * | 3/1991 | Johnson | ................. | A61J 1/2096 |
| | | | | 604/240 |
| 5,312,380 A * | 5/1994 | Alchas | ................. | A61F 2/062 |
| | | | | 604/319 |
| 5,474,675 A * | 12/1995 | Kupka | ................. | B01D 29/018 |
| | | | | 210/224 |
| 7,101,354 B2 * | 9/2006 | Thorne, Jr. | ....... | A61M 5/31596 |
| | | | | 604/191 |
| 2001/0037091 A1 * | 11/2001 | Wironen | ........... | A61B 17/8816 |
| | | | | 604/236 |

(Continued)

*Primary Examiner* — Jill A Warden
*Assistant Examiner* — Brittany I Fisher
(74) *Attorney, Agent, or Firm* — Chan Hubbard PLLC; Keala Chan (57) ABSTRACT

A syringe system for harvesting, mixing and emulsifying lipoaspirate and for further harvesting stromal vascular faction of adipose tissue. Stromal vascular faction contains mesenchymal stem cells, which have medically therapeutic uses. A mixing and/or emulsifying apparatus can be reciprocated in a syringe and combined with the stopper of the syringe, so that the syringe can be multi-purpose for harvesting, mixing, emulsifying, centrifuging, and transferring. This system minimizes transfers between syringes, allowing the system to remain closed and sterile.

11 Claims, 7 Drawing Sheets

(56) References Cited

U.S. PATENT DOCUMENTS

| | | | |
|---|---|---|---|
| 2005/0123895 A1* | 6/2005 | Freund | A61B 17/32002 435/2 |
| 2006/0178626 A1* | 8/2006 | Axelsson | A61M 5/322 604/110 |
| 2009/0062740 A1* | 3/2009 | Thorne, Jr. | A61M 5/284 604/191 |
| 2009/0131864 A1* | 5/2009 | Pickhard | A61M 5/284 604/83 |
| 2010/0112084 A1* | 5/2010 | Wu | C12N 5/0653 424/574 |
| 2010/0318063 A1* | 12/2010 | Soll | A61M 5/19 604/518 |
| 2011/0046602 A1* | 2/2011 | Grimm | A61M 5/284 604/506 |
| 2011/0166596 A1* | 7/2011 | Delmotte | A61J 1/2096 606/214 |
| 2012/0136298 A1* | 5/2012 | Bendix | A61M 5/2448 604/89 |
| 2012/0184920 A1* | 7/2012 | Okihara | A61M 5/1452 604/222 |
| 2012/0265171 A1* | 10/2012 | Thorne, Jr. | A61M 5/31596 604/518 |
| 2012/0271254 A1* | 10/2012 | Schafer | A61M 1/0005 604/319 |
| 2013/0158515 A1* | 6/2013 | Austen, Jr. | A61M 5/14526 604/522 |
| 2014/0363891 A1* | 12/2014 | Llull | C12M 45/09 435/378 |
| 2015/0118752 A1* | 4/2015 | Cimino | C12N 5/0653 435/379 |
| 2016/0030486 A1* | 2/2016 | Cimino | C12M 45/02 424/93.7 |
| 2016/0208211 A1* | 7/2016 | Cimino | C12M 47/04 |

* cited by examiner

SYSTEM AND METHOD FOR HARVESTING EMULSIFIED FAT AND STEM CELLS

CROSS-REFERENCE TO RELATED APPLICATION

This application is a divisional of U.S. patent application Ser. No. 14/846,357, which claims the benefit of 62/045,925, with priority date Sep. 4, 2014.

FIELD OF THE INVENTION

The invention lies in the field of fat processing, in particular in the field of medical devices.

BACKGROUND

Fat grafting is a widely implemented surgical procedure, and in the cosmetic context is commonly known as lipofilling. Typically, lipoaspirate harvested during liposuction is cleaned and injected subdermally for cosmetic filling or to treat trauma or aging. Some surgeons prefer to further emulsify the harvested lipoaspirate for intradermal injection with finer needles, for instance in delicate facial areas. It has also been suggested that emulsification may sufficiently break down fat cells thus yielding the stromal vascular fraction of the adipose tissue. See, e.g., Tonard et al., *Nanofat Grafting: Basic Research and Clinical Applications,* 132(4) Plast Reconstr Surg 1017-26 (2013). This stromal vascular fraction (SVF) contains mesenchymal stem cells, as well as endothelial cells, monocytes, macrophages, granulocytes, and lymphocytes.

Emulsification may be performed by shifting lipoaspirate between two syringes connected by a syringe transfer. This procedure strains the hands and a more efficient device that can be used in a sterile environment is needed.

SUMMARY

The invention is a mixing apparatus operable to be reciprocated in a vessel such as a syringe barrel for simple mixing without strain, and furthermore operable to combine with the stopper of the syringe so that transfers are minimized and the system remains closed and sterile. In particular, an emulsifying apparatus is described that efficiently breaks down adipocytes with a few strokes of the syringe shaft while maintaining the integrity of the SVF cells. The mixing and emulsifying apparatuses have uses in many applications in which mixing, emulsification and transfer are desired.

DETAILED DESCRIPTION

Figure 1A:
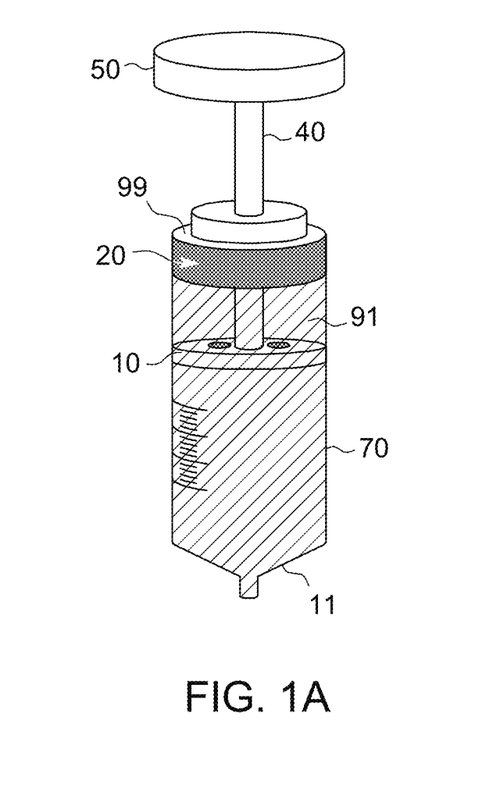
FIG. 1A depicts a full view of the device of the present invention being used to mix fluid within a syringe barrel.
Figure 1B:
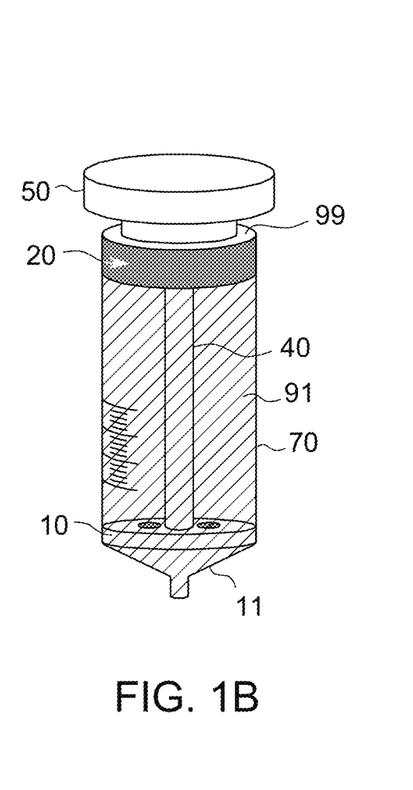
FIG. 1B depicts a full view of the device of the present invention being used compatible with some centrifuges.
Figure 1C:
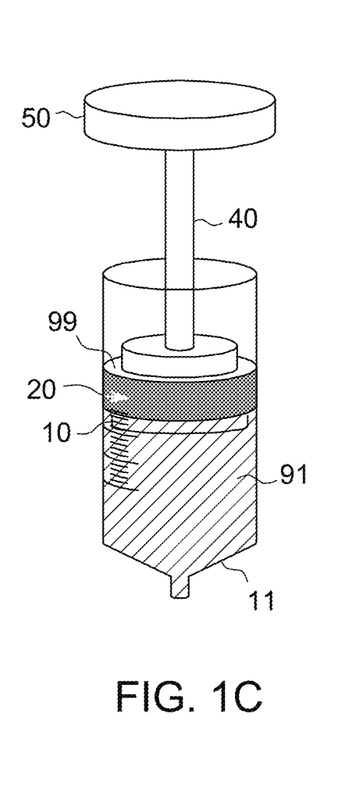
FIG. 1C depicts a full view of the device of the present invention being used as a syringe.

The invention will be described in an exemplary environment of use as shown in FIGS. 1A through 1C. In the syringe pictured, a mixing apparatus 10 is stroked, in one or more reciprocating motions, through fluid 91 while stopper 20 remains fixed at proximal end 99 of the syringe barrel 70. In this example fluid 91 is harvested lipoaspirate such as from a liposuction procedure, but the fluid can be any fluid that requires mixing or emulsification, including but not limited to food products and cosmetic creams. Similarly, while a syringe is pictured for purposes of the example, the device is not necessarily limited to medical uses or even cylindrical vessels. The point is that the mixing apparatus substantially fills a transection of the vessel so that fluid travels through the mixing apparatus rather than around the sides of the apparatus, and, as shown in FIG. 1C, the mixing apparatus 10 is further operable to be engaged with stopper 20 so that fluid can be expelled from the syringe. Thus, the device can be used in any application in which a combination of mixing, suction and extrusion is desired.

Figure 2:
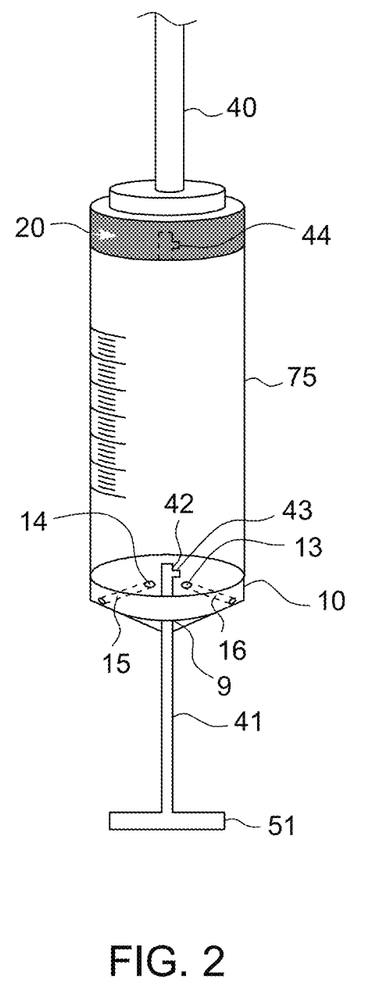
FIG. 2 depicts an embodiment wherein the mixing apparatus and the stopper are on separate shafts.

The configuration of shaft, stopper and mixing apparatus need not be on a single apparatus. In particular, as shown in FIG. 2, the mixing apparatus 10 may be attachable to a first shaft 41, and the stopper 20 may be coupled to a second shaft 40, wherein the mixing apparatus is operable to be reciprocated using the first shaft 41, while stopper 20 remains at the proximal end and may be operated in a standard fashion after removal of shaft 41. The shaft 41 and mixing apparatus 10 may be attachable by any mechanical method known in the art, such as the threaded connection 9 of the preferred embodiment. In the example depicted, and the details of which will be further described below, mixing apparatus 10 may be a concave emulsifying disc having a partial shaft 42 extending from its proximal surface and acting as an obstacle for fluid flow, maximizing impact and therefore emulsification. Partial shaft 42 may also be engaged with stopper 20 by the bayonet pin 43, received in bayonet receiver 44 in stopper 20, in order to engage the mixing apparatus to the stopper. As currently exists in the art, stopper 20 may comprise internal connectors such as crowns in order to facilitate maneuverability of connectors and shafts. It should be evident that in some cases shaft 41 may also be detached and the stopper operated without being engaged to mixing apparatus, to manipulate fluid in the barrel, due to channels 15 and 16. This example is illustrative of another closed system that may be used in harvesting emulsified lipoaspirate, where washed or harvested lipoaspirate is transferred through the distal ends of a first syringe and into a mixing syringe 75 via a syringe transfer shaft, which is then disconnected and replaced with the reciprocating shaft 41. After mixing apparatus 10 is reciprocated, shaft 41 is then detached and removed, leaving the mixing syringe 75 filled with washed or emulsified lipoaspirate for further use.

The mixing apparatus 10 can be any desired apparatus for mixing. O-ring attachments may be used to further ensure a tight seal. In the preferred embodiment, depicted in FIG. 3, the mixing apparatus is a concave disc-shaped emulsifying apparatus comprising one or more channels 15 and 16, such that as the emulsifying disc is pushed to the distal end, fluid enters apertures 11 and 12, travels through channels 15 and 16, and exits apertures 13 and 14 to collide with shaft 40, an impact surface that acts as an obstacle to fluid flow. When the emulsifying disc is pulled proximally, fluid enters apertures 13 and 14, travels through channels 15 and 16, and exits apertures 11 and 12 to collide with the wall of the syringe barrel 70, a second impact surface acting as an obstacle to fluid flow. This emulsifying disc maximizes fluid collision with impact surfaces—here, the shaft and the barrel wall—such that emulsification is obtained in a minimum number of strokes.

Figure 3:
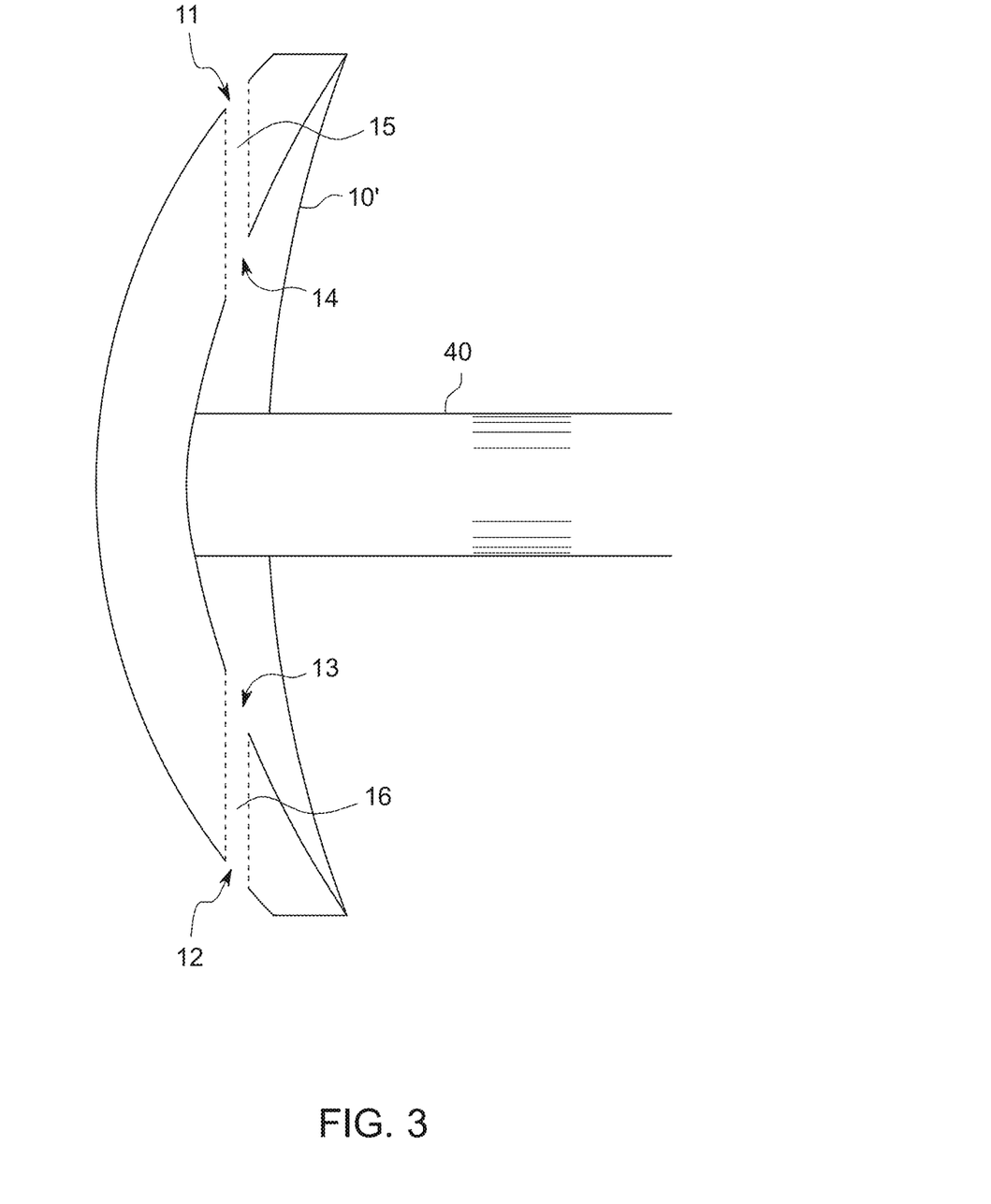
FIG. 3 depicts a cross-section of a preferred embodiment of the emulsifying apparatus of the present invention.

For lipoaspirate in 60 cc syringes, the preferred diameter of the channel is 1.5 mm, but can range from 0.5 mm to 2 mm, and likewise, the size of the apertures may vary. It will be apparent to those of ordinary skill that in a concave disc-shaped embodiment, the diameter of the apertures is greater than that of the channel, further increasing the pressure on the fluid as it travels through. It follows that the channels may comprise further fluid flow obstacles such as paths that maximize impact, or additional cutting, mixing, or straining mechanisms. Certain features of the emulsifying apparatus, such as the shape of the plate and the direction of channels, depend on the shape of the vessel in which it is being used, and as such can be determined by one of ordinary skill, so long as fluid flow obstacles and thus impact surface collisions are maximized in the manner described herein.

Figure 4A:
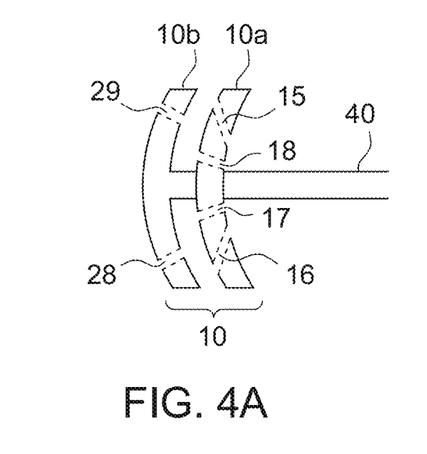
FIG. 4A is a side view of an alternative embodiment of an emulsifying apparatus.
Figure 4B:
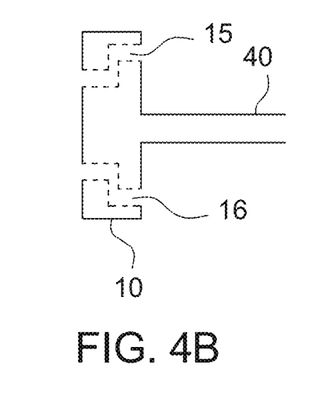
FIG. 4B is a side view of an alternative embodiment of an emulsifying apparatus.
Figures 4C, 4D:
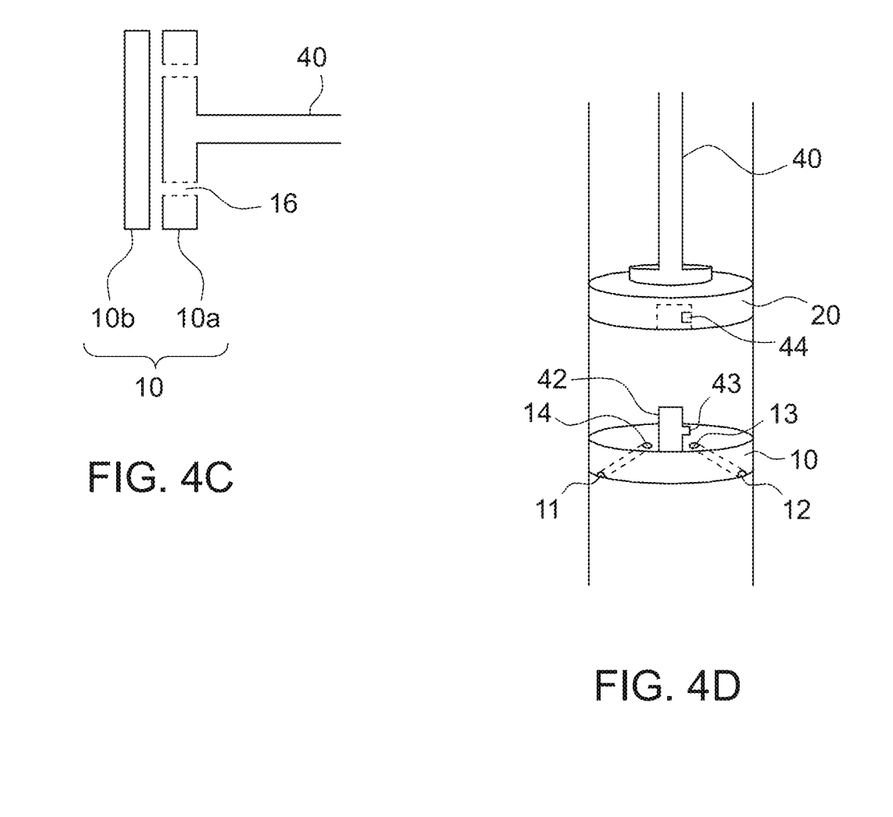
FIG. 4C is a side view of an alternative embodiment of an emulsifying apparatus.
FIG. 4D is a side view of an alternative embodiment of an emulsifying apparatus.

Examples of alternative emulsifying apparatuses are shown in FIGS. 4A through 4D. For instance, as shown in FIG. 4A, the emulsifying apparatus may be the combination of two emulsifying apparatus 10a and 10b, wherein channels 15, 16, 17, 18, 28 and 29 direct fluid such that in addition to fluid flow obstacles shaft and vessel wall, each emulsifying apparatus acts as a fluid flow obstacle to the other, maximizing impact surfaces and emulsification. FIG. 4B shows an emulsifying apparatus 10 wherein the fluid flow obstacle is inherent in the shape of channels 15 and 16, which may change directions to maximize impact surfaces and emulsification. Other types of fluid flow obstacles within the channel such as a straining blockage may also be used. FIG. 4C depicts an emulsifying apparatus comprised of a disc 10a attachable to shaft 40 and having channels 15 and 16, and a floating disc 10b that acts as a fluid flow obstacle when the emulsifying apparatus is pushed in a single direction. The floating obstacle may be any shape, for instance if disc 10a is a concave disc, they may be ball bearings that rest in the concave part of the disc, blocking the apertures. Furthermore, as shown in FIG. 4D, emulsifying apparatus 10 may be fixed within the vessel walls, such that fluid flow is caused by operation of stopper 20. The fluid flow obstacle may also be another stream of fluid. For instance, as shown in FIG. 2 and FIG. 4D, one of ordinary skill in the art will also note that even without partial shaft 42, when apertures 13 and 14 are directed towards each other, fluid emerging from one channel 15 acts as a flow obstacle to fluid emerging from the other channel 16, maximizing impact and therefore emulsification.

Figures 5, 6:
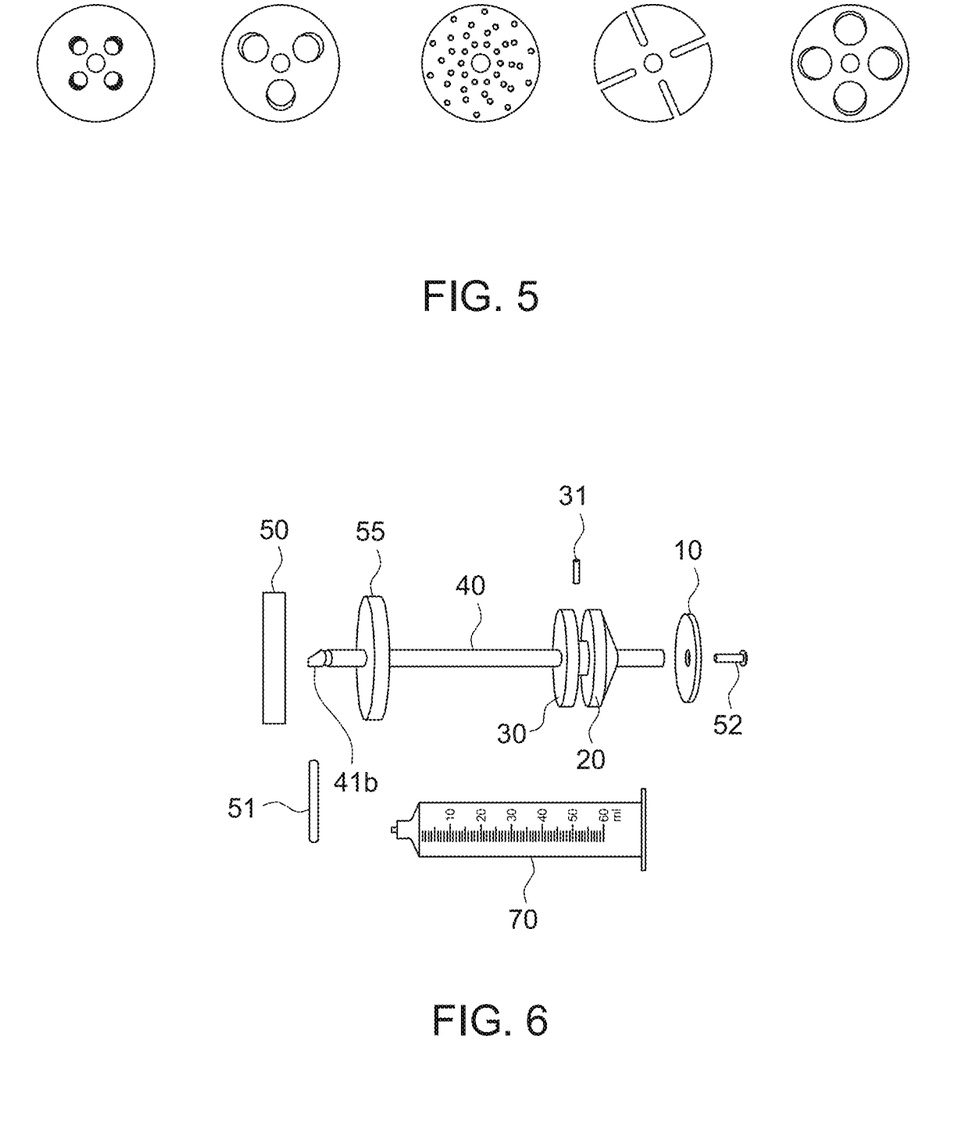
FIG. 5 depicts frontal views of sample varieties of washing discs that may be used with the present invention.
FIG. 6 is a full view of a disassembled embodiment of the invention.

Mixing apparatus 10 can have multiple purposes and can be interchangeable as desired. For instance, a simple disc for maximizing turbulence could be used for washing lipoaspirate with a sterile solution. Examples of washing discs are shown in FIG. 5. A mixing apparatus that is interchangeable may be desirable for many reasons, including, but not limited to, ease of manufacturing and user configurability. An example of a construction of the device with syringe barrel 70, shaft 40, attachable mixing apparatus 10 with screw 52, stopper 20 and crown 30, bayonet lock pin 31, cap 55, handle 50 and handle lock pin 51 is shown in FIG. 6. FIG. 6 is merely an illustrative example, wherein a bayonet lock is used to engage mixing apparatus 10 with stopper 20, and cap 55 and crown 30 engagement is used to fix stopper 20 at the proximal end of the barrel while mixing apparatus 10 is reciprocated. As noted herein, other methods of engaging mixing apparatus 10 to stopper 20 may be implemented by those of ordinary skill. For instance, using a nested shaft system, an inner shaft may be used to reciprocate the mixing apparatus while the outer shaft may be used to operate the stopper.

As is currently available in the art, different configurations of the syringe may enable its placement in a centrifuge. For example, in a procedure for processing lipoaspirate, it may be desirable to separate fat from blood and various other impurities, which can then be aspirated or otherwise removed. For instance, as depicted in FIG. 1B the mixing apparatus 10 and handle 50 are fully depressed. In an alternative embodiment, shaft 40 may be disconnectable from the stopper entirely by the use of a quick-release crown.

As will be evident to those of ordinary skill in the art, the teachings of the invention may be applied to the emulsification of lipoaspirate within a single syringe, followed by an efficient and sterile transfer after the emulsification apparatus is engaged with the stopper. As will also be known to those of ordinary skill in the art, various attachments and adapters are available to be mounted onto the distal opening of the syringe for further application of the emulsified fluid, such as syringes for subdermal injection, straining attachments to remove remaining connective tissue, and adaptors for transferring the emulsified fluid to a further chamber.

Figure 7:
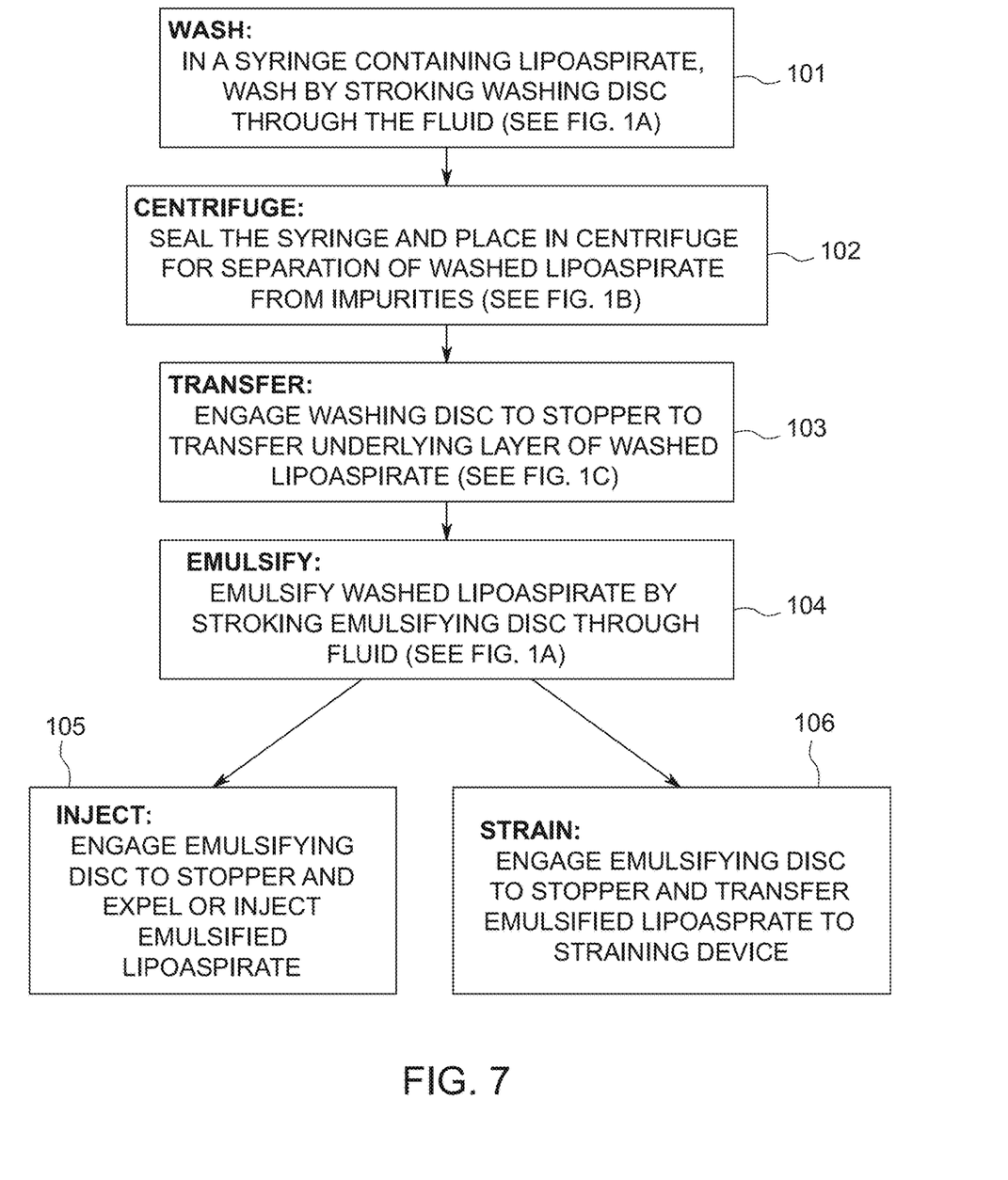
FIG. 7 is a flow-chart showing a method using the present invention.
Figure 8:
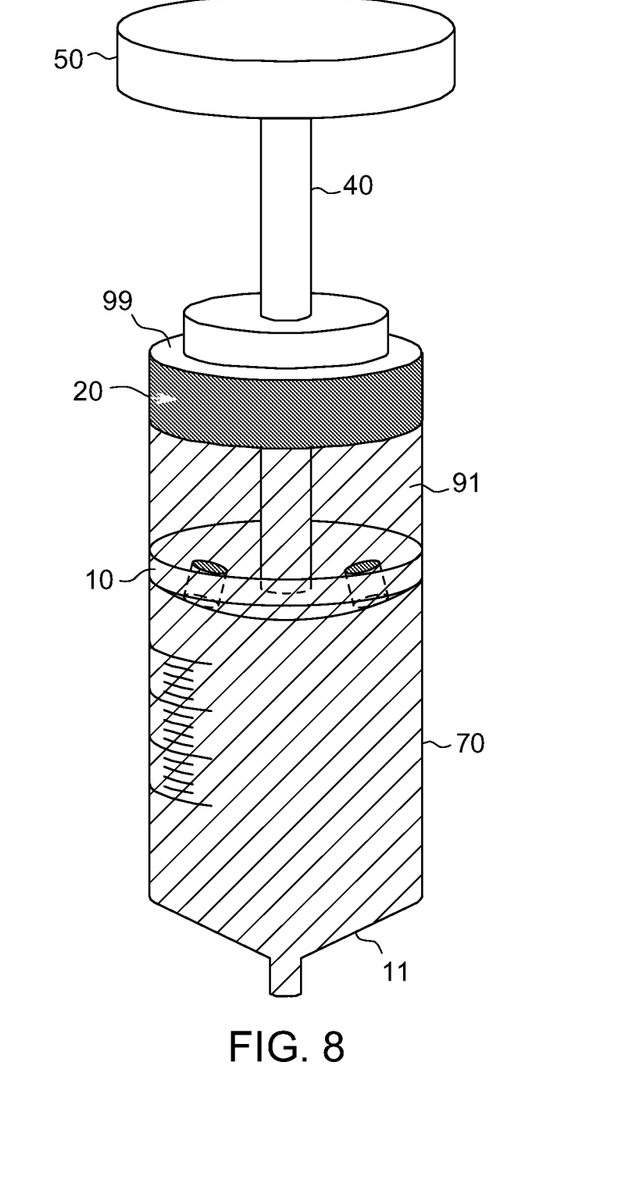
FIG. 8 is an elevated view of an emulsifying syringe described by the present invention.

Thus, the devices and apparatuses of the present invention lend themselves to use in a flexible and efficient method for harvesting an emulsified lipoaspirate rich in mesenchymal stem cells. As detailed in FIG. 7, the steps of an exemplary method may comprise: (1) washing 101 lipoaspirate and saline by stroking a washing disc through the fluid (see, e.g., FIG. 1A); (2) centrifuging 102 the washed lipoaspirate and removing impurities (see, e.g., FIG. 1B); (3) transferring 103 the washed lipoaspirate by engaging the washing disc to the syringe stopper and transferring the washed lipoaspirate to an emulsifying syringe, preferably by using a sealed syringe transfer; (4) emulsifying 104 the washed lipoaspirate by stroking an emulsifying disc through the fluid (see, e.g., FIG. 1A); (5) engaging the emulsifying disc to the stopper and either injecting 105 or straining 106 the emulsified lipoaspirate. It will be noted that an emulsifying apparatus enables in particular steps 104 and 105/106, just as a washing apparatus in particular enables steps 101 and 103, and that the emulsifying 104 and expelling 105/106 steps are the steps comprising the preferred embodiment of the method. The process may be executed in a single outpatient appointment contemporaneous with a liposuction procedure resulting in harvested lipoaspirate, and the devices and apparatuses of the present invention enable an entirely closed and sterile system optimized for medical use. It will further be noted that the devices and apparatuses of the present invention may be used in many contexts within and outside of the medical field, particularly in any context in which mixing or emulsifying within a syringe vessel is desired. It is contemplated that the invention and its method of use would be applicable in fields such as the development of cosmetic treatments and any other chemical laboratory use, or the mixing of creams and dressings in home and professional kitchens.

What is claimed is:

1. An apparatus for harvesting stromal vascular faction comprising:
   an emulsifying syringe comprising a shaft, a stopper, and an emulsifying apparatus, wherein the emulsifying apparatus comprises a concave disc that substantially fills a transection of the emulsifying syringe, and wherein the emulsifying apparatus comprises a first surface, a second surface, a channel, having a first aperture on the first surface and a second aperture on the second surface, for accommodating a flow of fluid through the channel, and a fluid flow obstacle such that the flow of fluid through the channel collides with the fluid flow obstacle;
   wherein the emulsifying apparatus is coupled to the shaft and operable to (a) be reciprocated through fluid in the emulsifying syringe and (b) be engaged to the stopper, and wherein the stopper is operable to intake or expel fluid from the emulsifying syringe.

2. The apparatus of claim 1 wherein the fluid flow obstacle is the shaft.

3. The apparatus of claim 1 further comprising
   a washing syringe comprising a shaft, a stopper, and a mixing apparatus attachable to the shaft and operable to (a) be reciprocated to mix a fluid within the washing syringe and (b) be engaged with the stopper of the washing syringe, wherein said stopper is operable to intake or expel fluid from the washing syringe; and
   a syringe transfer for transferring fluid from the washing syringe to the emulsifying syringe.

4. An apparatus for harvesting stromal vascular faction comprising:
   a washing syringe comprising a shaft, a stopper, and a mixing apparatus attachable to the shaft of the washing syringe and operable to (a) be reciprocated to mix a fluid within the washing syringe and (b) be engaged with the stopper of the washing syringe, wherein said stopper of the washing syringe is operable to intake or expel fluid from the washing syringe;
   an emulsifying syringe comprising a shaft, a stopper, and an emulsifying apparatus, wherein the emulsifying apparatus comprises a concave disc that substantially fills a transection of the emulsifying syringe, wherein the emulsifying apparatus comprises a first surface, a second surface, a channel, having a first aperture on the first surface and a second aperture on the second surface, for accommodating a flow of fluid through the channel, and a fluid flow obstacle such that the flow of fluid through the channel collides with the fluid flow obstacle, and the emulsifying apparatus is coupled to the shaft of the emulsifying syringe and operable to (a) be reciprocated through fluid within the emulsifying syringe and (b) be engaged to the stopper of the emulsifying syringe, and wherein the stopper of the emulsifying syringe is operable to intake or expel fluid from the emulsifying syringe; and
   a syringe transfer for transferring fluid from the washing syringe to the emulsifying syringe.

5. The apparatus of claim 4 wherein the fluid flow obstacle is the shaft of the emulsifying syringe.

6. A method for harvesting stromal vascular fraction in an emulsifying syringe comprising:
   reciprocating an emulsifying apparatus through a washed lipoaspirate to obtain emulsified lipoaspirate;
   engaging the emulsifying apparatus to a stopper; and
   depressing the stopper to expel the emulsified lipoaspirate.

7. The method of claim 6 further comprising the step of attaching a straining filter to the emulsifying syringe; and obtaining stromal vascular faction by depressing the stopper of the emulsifying syringe to expel the emulsified lipoaspirate through the straining filter.

8. The method of claim 6 further comprising the steps of:
   reciprocating a washing apparatus through a lipoaspirate in a washing syringe to obtain the washed lipoaspirate;
   attaching a syringe transfer to the washing syringe and the emulsifying syringe; and
   transferring the washed lipoaspirate to the emulsifying syringe.

9. The method of claim 8 further comprising the step of attaching a straining filter to the emulsifying syringe; and obtaining stromal vascular faction by depressing the stopper of the emulsifying syringe to expel the emulsified lipoaspirate through the straining filter.

10. The method of claim 9 further comprising the steps of placing the washing syringe in a centrifuge to separate layers of washed lipoaspirate and impurities; and removing the impurities from the washing syringe.

11. The method of claim 8 further comprising the steps of placing the washing syringe in a centrifuge to separate layers of washed lipoaspirate and impurities; and removing the impurities from the washing syringe.

* * * * *